United States Patent [19]

Sharpe

[11] Patent Number: 4,539,976

[45] Date of Patent: Sep. 10, 1985

[54] ENDOSCOPIC SURGICAL INSTRUMENT

[76] Inventor: Jewett M. Sharpe, 201 Wood Rd., Richmond, Va. 23229

[21] Appl. No.: 578,037

[22] Filed: Feb. 8, 1984

[51] Int. Cl.³ .............................................. A61B 1/00
[52] U.S. Cl. ...................................... 128/6; 128/305; 128/754
[58] Field of Search ....................... 128/4, 6, 3, 5, 751, 128/752, 754, 305, 305.3

[56] References Cited

U.S. PATENT DOCUMENTS

| 1,483,085 | 2/1924 | Heidbrink | 128/305 |
|---|---|---|---|
| 1,493,240 | 5/1924 | Bohn | 128/305 |
| 1,663,761 | 3/1928 | Johnson | 128/305 |
| 2,729,210 | 1/1956 | Spencer | 128/751 |
| 3,013,553 | 12/1961 | Averbach | 128/2 |
| 3,857,384 | 12/1974 | Watson | 128/2 B |
| 3,924,608 | 12/1975 | Mitsui | 128/6 X |
| 3,989,033 | 11/1976 | Halpern et al. | 128/754 |
| 4,055,167 | 10/1977 | Bernstein | 128/2 B |
| 4,177,797 | 12/1979 | Baylis et al. | 128/754 |
| 4,372,295 | 2/1983 | Heckele | 128/6 X |

Primary Examiner—William H. Grieb
Attorney, Agent, or Firm—Cushman, Darby & Cushman

[57] ABSTRACT

An instrument for surgical procedures is provided which comprises a hollow cannula for slidably receiving a cylindrical scalpel member which is slotted at one end. One side of the slot is ground to produce a cutting edge. The cannula is provided on its exterior with elements for adjustably supporting an elongated optical device which extends substantially parallel to the cannula.

7 Claims, 9 Drawing Figures

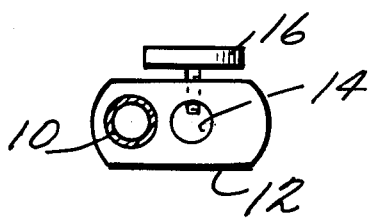
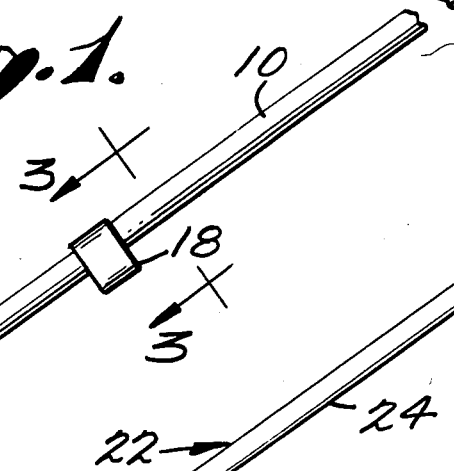
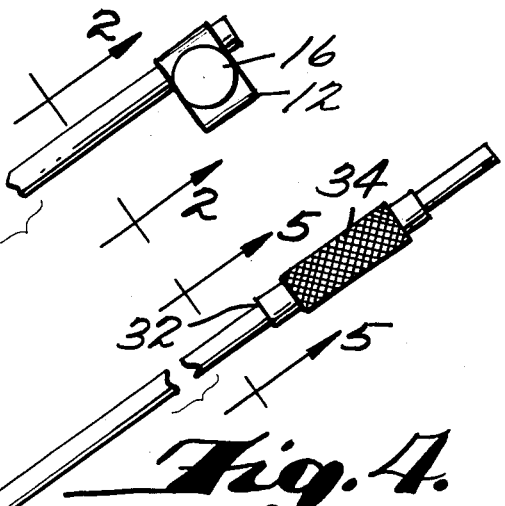
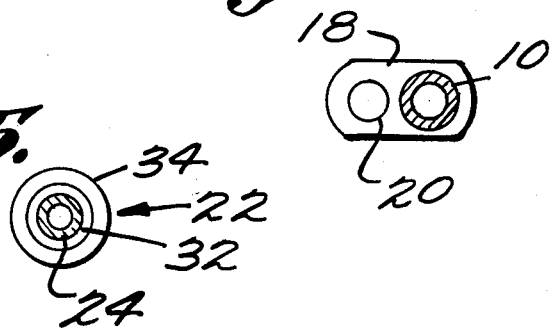
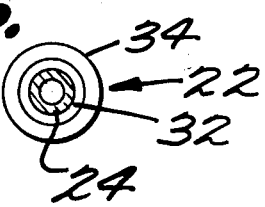
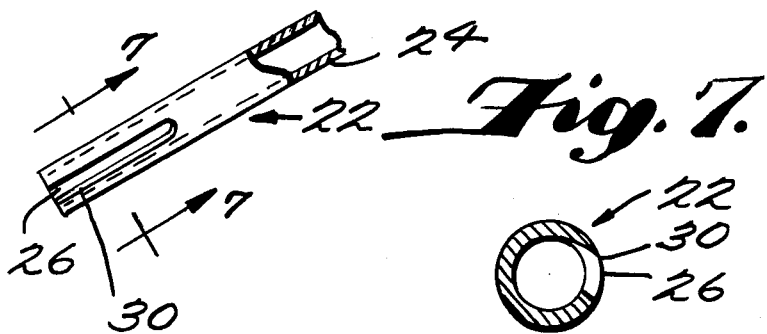
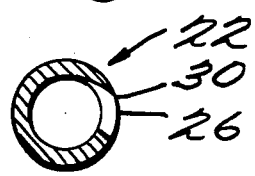

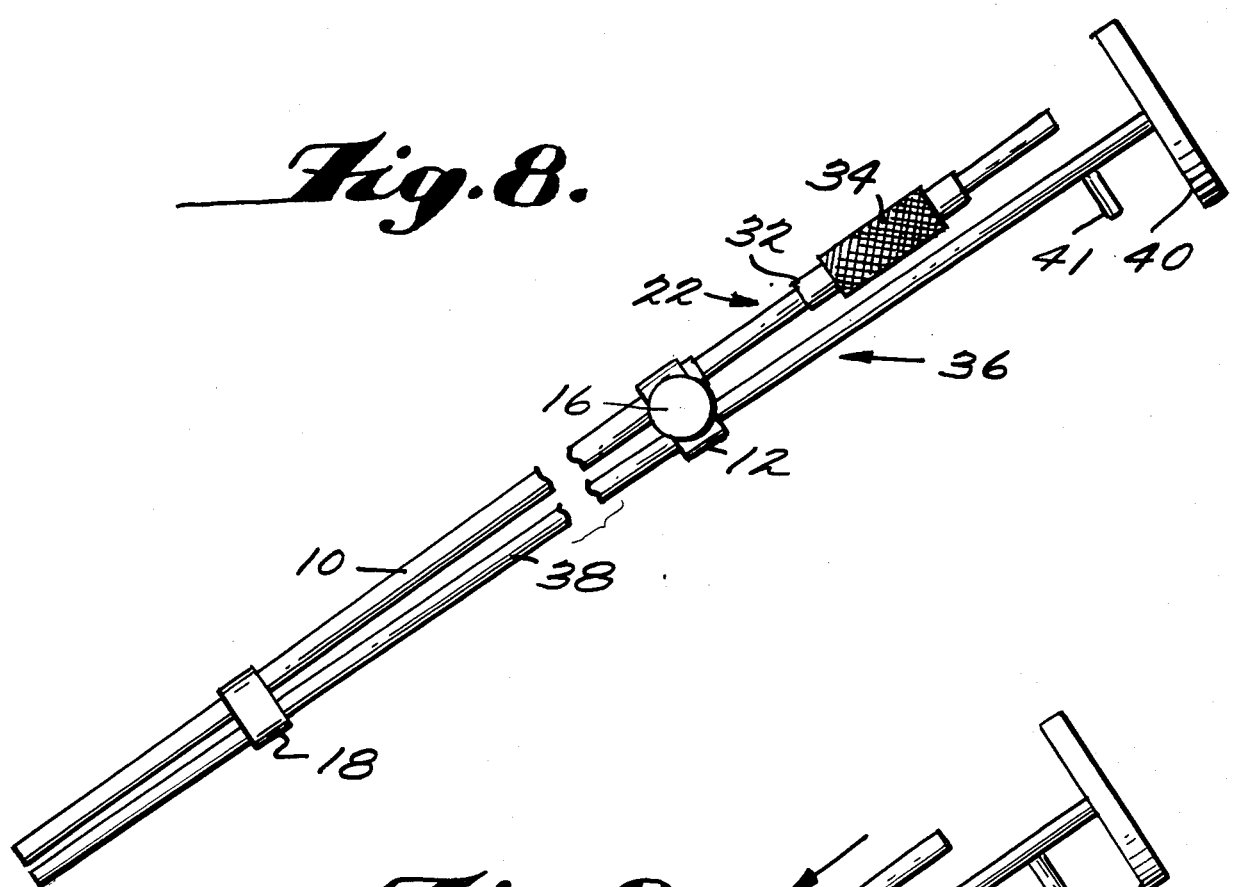
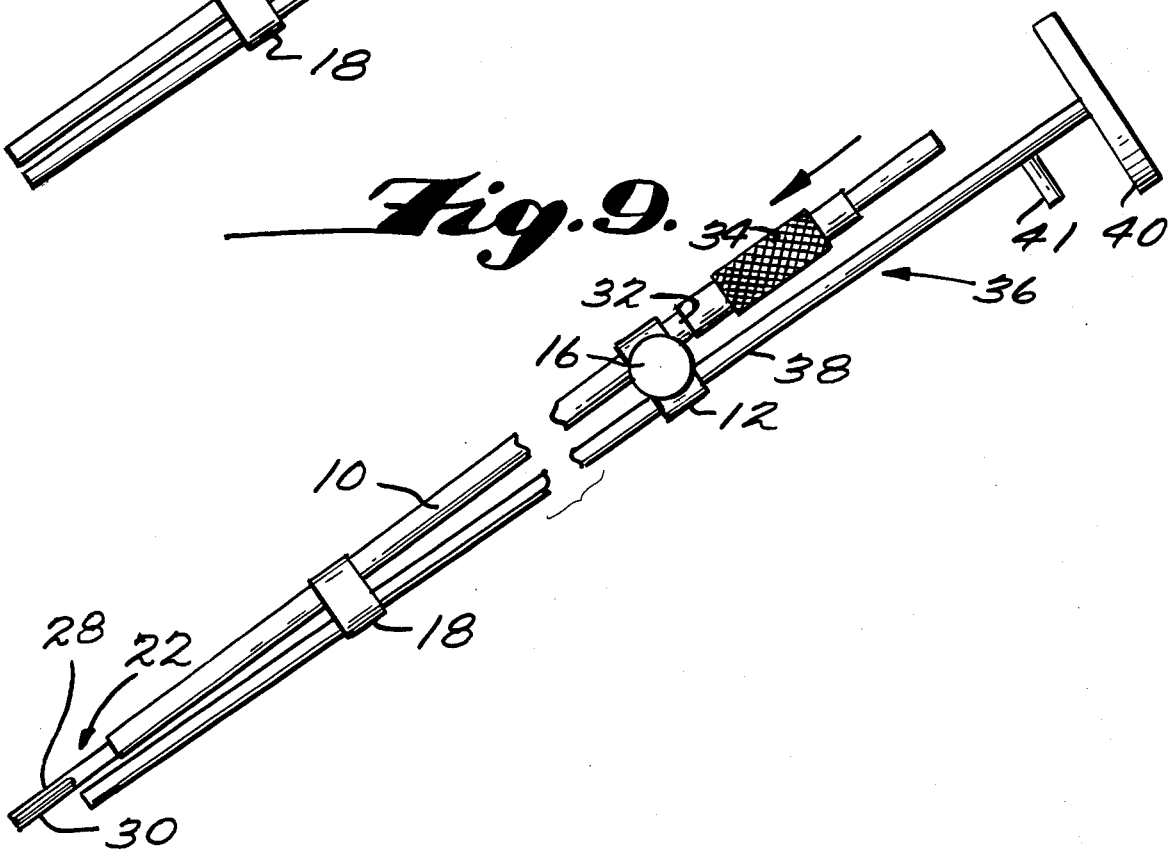

ENDOSCOPIC SURGICAL INSTRUMENT

BACKGROUND OF THE INVENTION

The present invention relates to apparatus particularly suitable for resection of tissue in the trachea in such conditions as subglottic stenosis and tracheal stenosis. The primary object of the invention is to provide a novel approach to the resection of such tissue by means of a semicylindrical scalpel associated with an optical device to allow visualization of the area being operated upon.

It is well recognized that the cricoid cartiliage, the narrowest portion of the pediatric airway, is quite sensitive to trauma of any form, especially the mechanical irritation of endotracheal intubation with the resultant formation of a stenotic and restrictive lesion. Because of the frequency of the problem and the difficulty in its management, several treatment modalities have been devised.

The original work to deal with this lesion was aimed at expanding the diameter of the cricoid with interposition grafts. With the advent of adequate visualization provided by the Hopkins rodlens telescope, however, endoscopic resection of the lesion of subglottic stenosis became more practicable. With the aid of this visualization, laser surgery, electrosurgery, and cryosurgery have been employed to resect this tissue.

In conjunction with cryotherapy, biopsy forceps advanced through the operating bronchoscope have been used to bite out small pieces of tissue. This is a time-consuming and technically difficult procedure which meets with limited success due to the fact that the frozen tissue is difficult to resect with the biopsy forceps, and also, the randomly ragged edges left after the procedure may not allow optimal tissue healing. There additionally is the likelihood of recurrent fibrosis.

The present invention was conceived and developed to provide a novel, useful, and improved surgical instrument, particularly, suitable for resection of subglottic stenosis and other tracheal lesions in conjunction with endotracheal cryotherapy, that could overcome the aforementioned problems associated with the cryotherapy and biopsy forceps modality. The instrument is a more mechanically advantageous device which, rather than biting small pieces of tissue, cuts readily through the fixed frozen tissue of the lesion thus requiring less time, fewer applications, and which, upon completion of the procedure, presents a smooth surface potentially more amenable to tissue healing and prevention of subsequent fibrosis than has previously been possible.

SUMMARY OF THE INVENTION

The surgical instrument according to the present invention comprises a hollow cannula provided with supports on its exterior wall for securing an elongated optical device thereto. A scalpel member is slidably received within the cannula. This member comprises an elongated cylindrical rod formed with a substantially U-shaped slot at one end thereof, a side of the slot being ground to produce a cutting edge. The length of the rod is such that the cutting edge may be extended beyond the end of the cannula or withdrawn within its interior.

DETAILED DESCRIPTION OF THE INVENTION

The invention now will be described in greater detail with respect to the accompanying drawings which illustrate a preferred embodiment of the invention and wherein:

FIG. 1 is a perspective view of a cannula which comprises a first component of the present invention;

FIG. 2 is an enlarged sectional view taken along line 2—2 of FIG. 1;

FIG. 3 is an enlarged sectional view taken along line 3—3 of FIG. 1;

FIG. 4 is a perspective view of a scalpel member which comprises a second component of the present invention;

FIG. 5 is an enlarged sectional view taken along line 5—5 of FIG. 4;

FIG. 6 is an enlarged fragmented view of a portion of the scalpel member illustrated in FIG. 4;

FIG. 7 is an enlarged sectional view taken along line 7—7 of FIG. 6;

FIG. 8 is a perspective view of the cannula and scalpel member combined in operative relationship, the cutting edge of the scalpel member being retracted within the cannula and the cannula supporting an optical device which comprises a third component of the present invention; and FIG. 9 is a perspective view corresponding to FIG. 8, but with the scalpel member's cutting edge exposed.

Referring to FIGS. 1-3, a cannula 10 is provided for receiving a scalpel member in a manner hereinafter to be described. The cannula comprises a rigid hollow cylinder. A first support element 12 is secured to one end of the cannula. Element 12 is provided with an aperture 14 extending parallel to the cannula's longitudinal axis. A clamping screw 16 passes through a wall of element 12 into aperture 14 for a purpose which will be detailed hereinafter.

Adjacent its opposite end, cannual 10 has secured thereto a second support element 18 provided with an aperture 20 axially aligned with aperture 14 of element 12.

FIGS. 4-7 illustrate a scalpel member 22 comprising an elongated hollow cylindrical element 24 having an outer diameter which is slightly less than the inner diameter of cannula 10. At one of its ends, the wall of element 24 is provided with a substantially U-shaped slot 26. One side of the slot is ground to produce a razor-like cutting edge 30 (FIG. 7) extending longitudinally of member 22.

Adjacent its opposite end, member 22 is provided with an annular shoulder 32. The distance between shoulder 32 and the ground cutting edge 30 is slightly greater than the length of cannula 10.

A knurled finger grip 34 is positioned on the opposite side of shoulder 32 from the slotted end of member 22.

Referring to FIGS. 8 and 9, an optical device 36 is supported by the cannula. More particularly, device 36 is a conventional fiber optics apparatus known as a Hopkins rod-lens telescope. This device includes an elongated cylindrical portion 38 for housing optical fibers. At its end, device 36 is provided with an eyepiece and an attachment for a light source, elements 40 and 41, respectively. Portion 38 is slidingly received within the aligned apertures 14 and 20 of support elements 12 and 18, respectively, and the clamping screw 16 is employed to selectively fix the optical device relative to the cannula.

The operative relationship between the components which have been described will be explained by reference to FIGS. 8 and 9.

In FIG. 8, the scalpel member 22 is slidably received within the cannula 10 in a position such that shoulder 32 is spaced from the end of the cannula. When so oriented, the cutting edge of member 22 is within the cannula and therefore is not exposed.

With the components arranged as shown in FIG. 8, the instrument is inserted into a patient's trachea. When properly positioned adjacent the area where tissue is to be resected, the optical device 36 is moved to the desired position for illuminating the operating area by releasing clamping screw 16 and displacing the device relative to the cannula 10. The screw then is tightened to fix device 36 at the selected location.

The surgical procedure is performed by sliding the scalpel member 22 along cannula 10 until shoulder 32 engages the end of the cannula, as shown in FIG. 9. When this occurs, the end of the member 22 bearing cutting edge 30 is exposed. Upon grasping the fingergrip 34 and rotating member 22, the ground cutting edge 30 is moved in a curved path to smoothly resect the tissue.

By joining an aspirator (not shown) to the end of the cylindrical cannula 10 adjacent grip 34, fluid and debris can be cleared from the operating area.

What is claimed is:

1. An endoscopic surgical instrument comprising:
   a hollow cylindrical cannula;
   a first support element secured to said cannula adjacent one of its ends;
   a second support element secured to said cannula adjacent the other end of its ends;
   an elongated optical device retained in substantially parallel relationship with the cannula by said support elements;
   a scalpel member operatively related to said cannula, said scalpel member comprising a cylindrical element slidably received within the cannula, said cylindrical element having a substantially U-shaped slot at one end extending longitudinally thereof, one side of said slot being ground to produce a cutting edge; and
   said scalpel member further comprising: a shoulder located adjacent the opposite end of said cylindrical element, the distance between the shoulder and said cutting edge being greater than the length of the cannula whereby when said shoulder engages an end of the cannula, the cutting edge is exposed; and gripping means located on the opposite side of the shoulder from the slotted end of the cylindrical element.

2. A surgical instrument as set forth in claim 1, wherein said cylindrical element is hollow.

3. A surgical instrument as set forth in claim 1, further comprising clamping means associated with one of said support elements for adjustably retaining the optical device.

4. A surgical instrument as set forth in claim 1, wherein said optical device includes fiber optics.

5. A surgical instrument as set forth in claim 3, wherein said cylindrical element is hollow.

6. A surgical instrument as set forth in claim 4, wherein said cylindrical element is hollow.

7. A surgical instrument as set forth in claim 6, further comprising clamping means associated with one of said support elements for adjustably retaining the optical device.

* * * * *